US006001119A

United States Patent [19]

Hampson et al.

[11] Patent Number: 6,001,119

[45] Date of Patent: Dec. 14, 1999

[54] COMPRESSION SYSTEM

[75] Inventors: David Mark Hampson, Cardiff; Heather Elizabeth Hutflesz, Gwent; Rolf Schild, London, all of United Kingdom

[73] Assignee: Huntleigh Technology, PLC, Bedfordshire, United Kingdom

[21] Appl. No.: 09/131,038

[22] Filed: Aug. 7, 1998

[51] Int. Cl.[6] .................................................... A61B 17/00

[52] U.S. Cl. ............................................. 606/202; 601/27

[58] Field of Search .................................... 606/201, 202, 606/203, 204; 601/27, 28, 29, 30, 31, 32, 151, 152; 128/DIG. 20

[56] References Cited

U.S. PATENT DOCUMENTS

| | | | |
|---|---|---|---|
| Re. 32,940 | 6/1989 | Gardner et al. . | |
| B1 Re. 32,940 | 12/1996 | Gardner et al. . | |
| 5,135,473 | 8/1992 | Epler et al. | 606/201 |
| 5,277,695 | 1/1994 | Johnson, Jr. et al. | 602/14 |
| 5,435,009 | 7/1995 | Schild et al. | 602/13 |
| 5,868,690 | 2/1999 | Eischen, Sr. | 601/151 |

*Primary Examiner*—Michael Buiz
*Assistant Examiner*—Jonathan D. Goldberg
*Attorney, Agent, or Firm*—Brown Raysman Millstein Felder & Steiner LLP

[57] ABSTRACT

A garment includes a compression system useful for stimulating venous and/or arterial blood flow in a limb, such as the foot or leg, by applying cyclic compressive pressures thereto. The garment has at least one inflatable bladder which is gradually inflated to slowly compress the foot substantially in the sole, the upper dorsi-medial areas, and dorsi-lateral areas of the foot, and then deflated to rapidly release the pressure. The muscle mass of the foot is thus squeezed and, upon sudden release, reactive hyperaemia is produced which increases arterial inflow, thus increasing venous flow in the foot and/or the leg thereof. The compression system may be used alone or in conjunction with a garment of similar structure, applied to other portions of the limb, such as the calf or thigh, for simultaneous or sequential stimulation of venous blood flow in the limb.

20 Claims, 3 Drawing Sheets

COMPRESSION SYSTEM

BACKGROUND OF THE INVENTION

This invention relates to a compression system to improve the circulation in a limb extremity, and more particularly, to a foot compression system.

DISCUSSION OF RELATED ART

It is known to increase or stimulate blood flow by using a compression system to apply compressive pressures to a limb extremity, e.g. a hand, thigh, calf or foot. The compressive pressures may be cyclic and may vary from providing a massaging action to a sharp pulse action.

It is generally believed that the foot is an effective site to apply compressive pressure. It has been shown that the arch of the foot houses a large venous plexus which normally is compressed by means of the foot extending and flattening the arch during walking or running thereby promoting circulation. U.S. Re. 39,420 shows a compression device which is said to use this phenomenon by providing a bladder only under the arch of the foot between the balls of the foot and the heel, which upon rapid inflation causes the arch to flatten to simulate the walking or running action. Other devices also exist which simply compress the arch of the foot by applying sharply pulsed, high pressures under the arch by means of an inflatable bag engaging the arch under the mid-foot in conjunction with or without similar devices on the calf and/or the thigh.

However, the known devices suffer from the disadvantage that the use of an inflatable bag located only under the arch results in uncomfortable squeezing of the foot due to the constricting shape; the foot has to adopt during inflation of the bag, causing pain to the patient so that the patient's compliance over prolonged use is poor. In addition, in order to provide an effective pumping pressure or flattening of the arch, very high pressures are needed to be applied rapidly directly onto the curve of the arch under the midtarsal region of the foot. This region of the arch is without any cushioning and the application of such pumping forces is painful and uncomfortable to the patient further adding to patient compliance difficulties.

SUMMARY OF THE INVENTION

We have discovered an effect on the circulation system that is dependent on compression of muscle, wherein release of the compression results in reactive hyperaemia which increases the arterial inflow thereby increasing venous outflow. We have found that this increase in venous flow is not dependent on venous priming.

According to the present invention, there is provided a garment for applying cyclic compressive pressures to a foot. The garment includes at least one bladder adapted to engage substantially the whole of the sole of the foot and also to engage longitudinally the dorsi-medial and dorsi-lateral areas of the top of the foot respectively, means adapted to locate and secure the garment to a foot, means to slowly inflate the bladder to provide a gradual compressive pressure to the sole and to the dorsi-medial and dorsi-lateral areas of a foot, followed by relatively rapid deflation of the bladder.

The garment of the invention applies compressive pressures to the muscle mass of a foot substantially over the whole of the sole and dorsum thereof, which application is very comfortable to the user. Due to the arrangement of the at least one bladder to cover the sole of the foot and the dorsum of the foot, the foot is not constricted sideways or stretched during inflation of the garment, as with prior art devices, but instead the foot lays flat and therefore avoids the pinching associated with the known devices. Moreover, in use, it is believed that the garment provides a complementary two-fold stimulation to the blood flow in the foot due to the dual application of compressive pressure on the muscle mass of the foot by the bladder under the sole as well as compressive pressure acting directly on the superficial veins underlying the dorsi-medial and lateral regions of the foot, the former enhancing arterial inflow due to hyperaemia and the latter serving to drive the blood from the veins of the foot.

An important benefit is that lower pressures are necessary to stimulate blood flow comparable to such blood flow achieved with prior art devices. The foot garment has been shown to have equivalent effect to the known sharply pulsed, high pressure devices in augmented blood velocity at the femoral vein. The biochemical effect is more complicated; for example, the fibrinolytic activity is enhanced and other factors such as the effect of circulating plasminogen activator, tissue plasminogen and other parameters are seen to combine to reduce the risk of clot formation.

Moreover, the lower pressures and slow inflation allow the use of a simpler pump to operate the foot garment.

Preferably, the garment includes only one bladder. Preferably, the bladder or bladders are inflated over a period of 2 seconds or more, to provide a slow rise in pressure, thereby avoiding any possible damage to the blood cells which may occur with the rapid high pressure rises in the prior art devices. Preferably, the inflation is held for a period of time before deflation, in the cycle, to further enhance arterial blood flow. In particular, the inflation is held for a period less or equal to the period of inflation.

Preferably, the bladder is made from vapor permeable material, and in particular, made of material having greater elasticity than the garment material so that the bladder provides a more effective transmission of pressure during inflation for any given pressure.

Preferably, the means for locating and securement of the garment include cushioning, for example, a foam backing. The cushioning, which may be, for example, foam prevents chafing and skin breakdown at the points of contact, which may be caused by the garment, when in use, pressing and rubbing against the skin surface during inflation and/or deflation of the bladder within, or by the garment being fitted tight around the foot.

In another aspect of the invention there is provided a garment for applying cyclic compressive pressures to a limb, with the garment including two sheets of plastic material joined together at their peripheries and joined internally to define at least one bladder, wherein the join line at the peripheries is located internally of the edge of the material/garment. The join line is set back and is located internal to the edge of the garment so that the join line avoids creating a hard edge on the garment, thereby preventing chafing of the skin at the points of contact, during use.

Preferably, the garment includes securing means, for example, hook-and-loop fasteners sold commercially as "VELCRO", joined at an edge of the garment.

Preferably, the garment includes through holes or apertures through the garment and bladder to provide ventilation to the limb, during use.

BRIEF DESCRIPTION OF THE DRAWINGS

Embodiments of the invention will now be described, by way of example, with reference to the accompanying drawings, in which.

DETAILED DESCRIPTION OF THE PREFERRED EMBODIMENTS

Figure 1A:
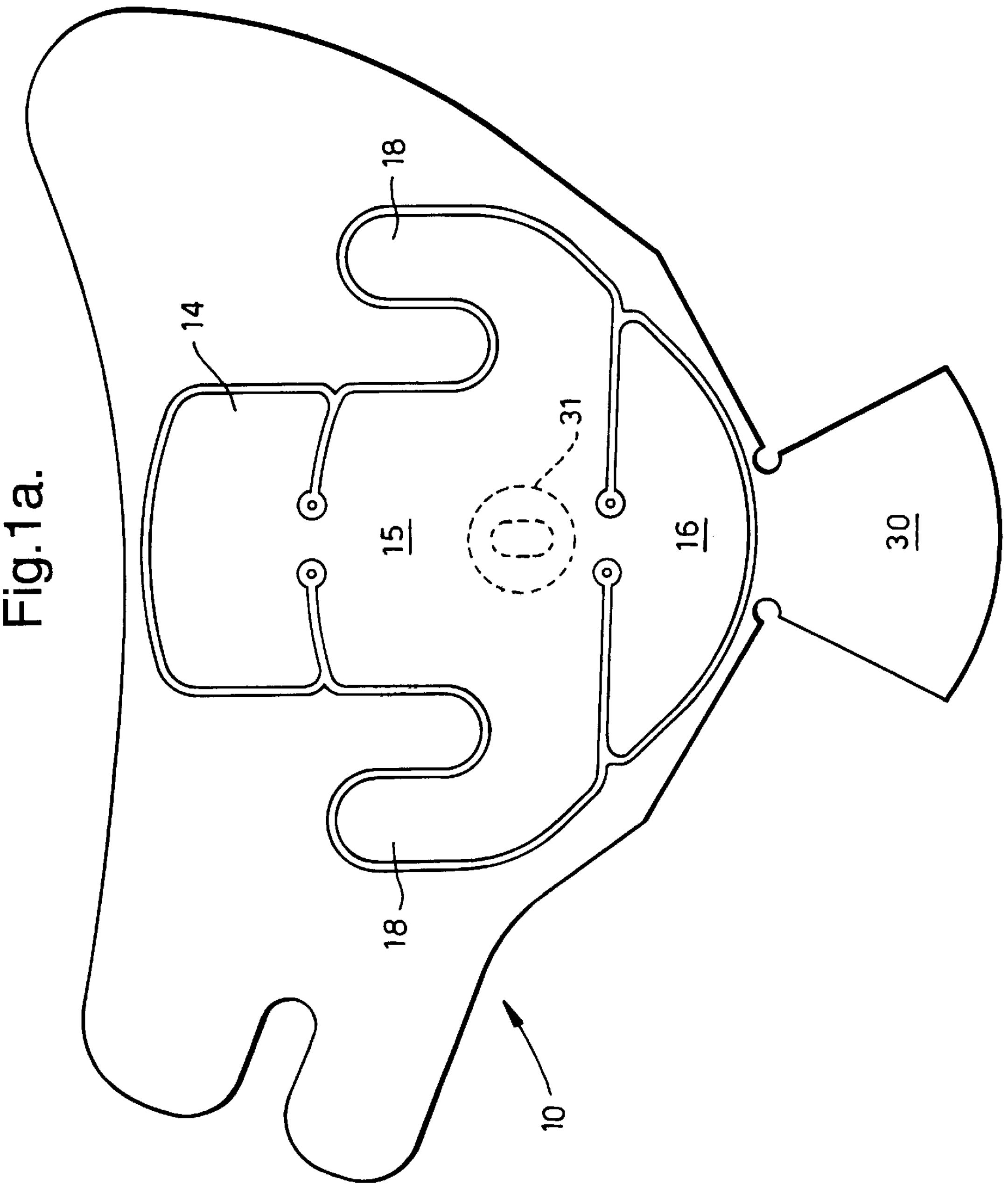
FIGS. 1*a* and 1*b* show plan views of garments according to the invention.
Figure 1B:
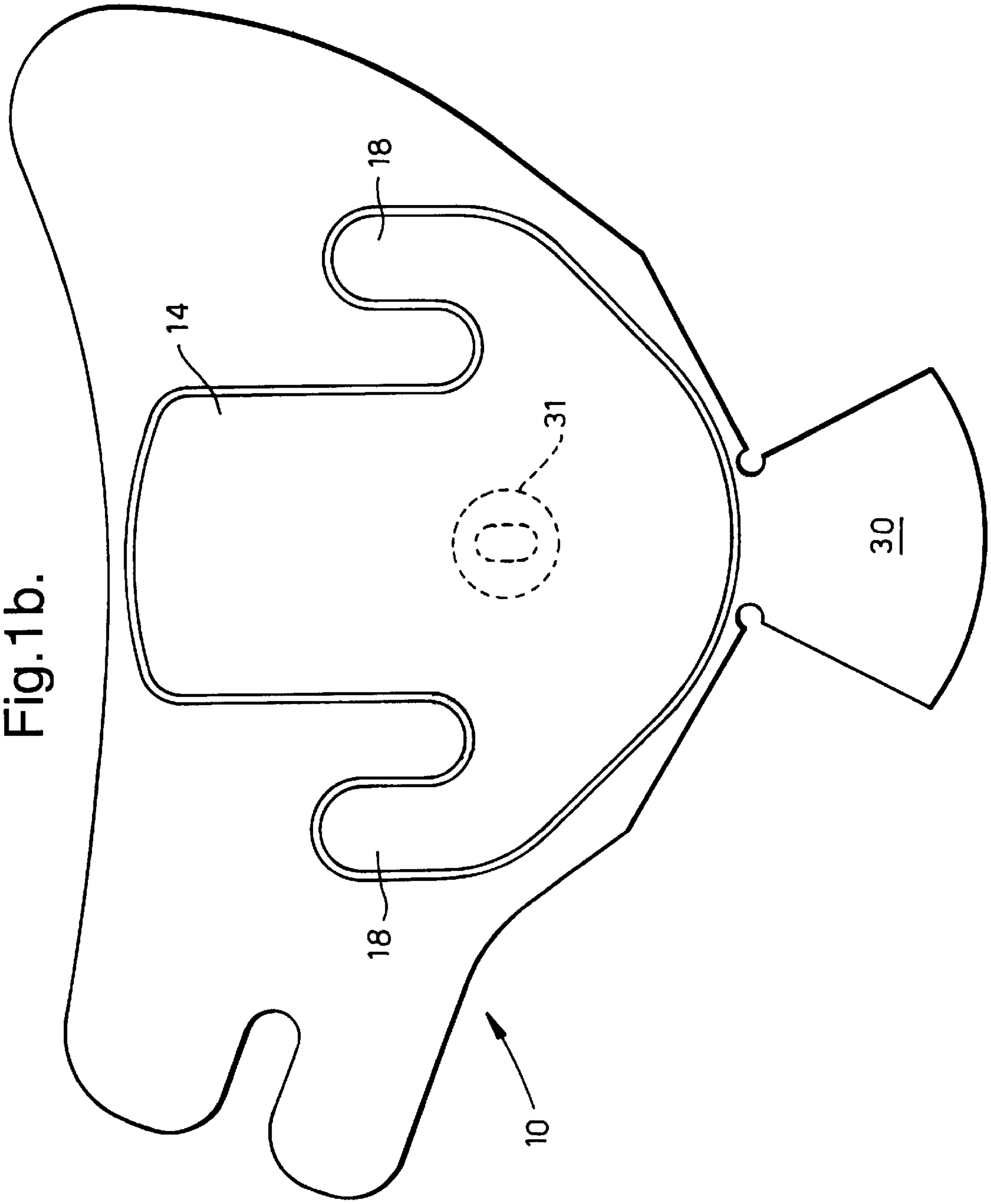
Figure 2:
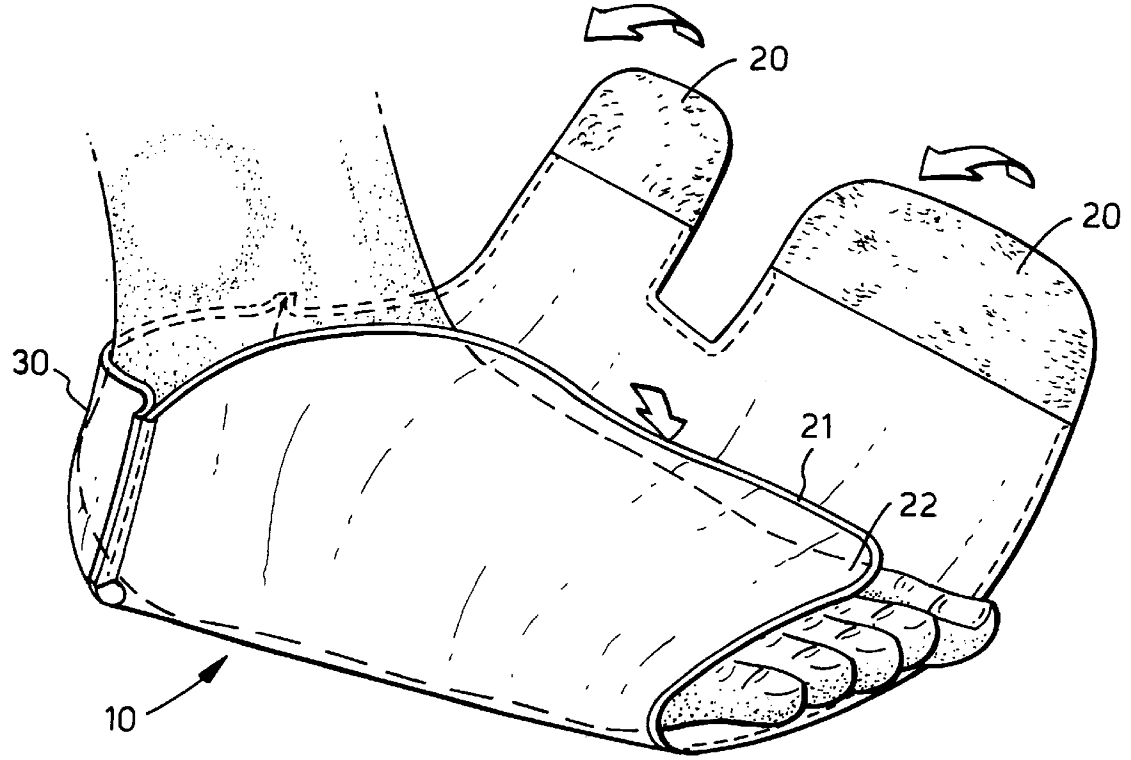
FIG. 2 is a perspective view of a garment as worn on a foot.

Referring to FIGS. 1*a* and 1*b* in conjunction with FIG. 2, a foot garment blank 10 is formed from two superposed sheets of plastic material 21 and 22. The inner material 21 is preferably more elastic than the outer material 22. The sheets 21, 22 are high-frequency welded together at their peripheries and internally in a pattern defining the bladders 14, 15, 16, 18 in one embodiment shown in FIG. 1*a,* or defining bladders 14, 18 in an alternative embodiment shown in FIG. 1*b*. The high-frequency weld is located internal to the peripheries of the garment so that a hard edge consisting of the two material layers and weld join is avoided. This peripheral weld which is set back internally provides a soft edge to the garment 22 which has been shown to minimise the problems of chafing at the points of contact known to occur with the prior art garments. The outer, less elastic material 21 is cut close to the peripheral weld line in order to allow only the softer more elastic material 22 edge to be in contact with the skin during use.

Conveniently, the high-frequency weld can be replaced by other available means for joining the materials, for example, ultrasonic welding, heat sealing or by adhesive bonding.

An aperture 31 is provided on the outer material for connection to a pressure source. A heel section 30 is further attached to opposing sides of the garment 10 to be positioned at a heel of a patient. To further add to the comfort of the user, the heel section includes a foam backing (not shown) to cushion the skin against chafing and skin breakdown at the heel sides during use of the garment.

As shown in FIGS. 2, the garment 10 is fitted to a Loot by positioning the heel of the foot of a patient against the heel section 30 and then the garment 10 is wrapped around the foot and held in place by suitable securing means, preferably cushioned in the heel section. The securing means may have, for example, hook-and-loop fastener 20 on their respective edges or other similar securing means. The hook-and-loop fasteners 20 is simply sewn or welded at one edge to an edge of the garment 10. The bladder surface may have through apertures (not shown) for ventilation of the foot during use.

Figure 3:
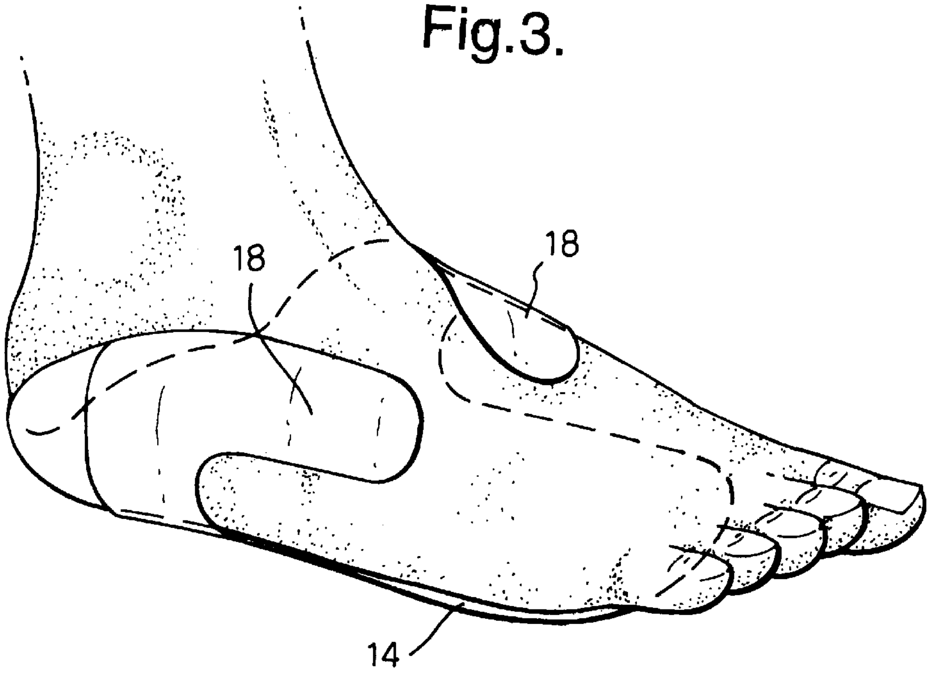
FIG. 3 is a schematic diagram of the bladder as shown FIG. 1*a* as arranged around the foot when the garment is worn as in FIG. 2.

In use, the at least one bladder 14, 15, 16, 18 within the garment 10 is inflated slowly, typically for 2.5 seconds by a pressure source of gas, such as air, to apply compressive pressures, typically up to a maximum of 130 mmHg, over substantially the whole of the sole of the foot as well as the dorsi-medial and dorsi-lateral areas of the foot. The bladder, in use, is shown in FIG. 3. This gradual compression of the sole and dorsum regions of the foot is believed to stimulate the flow of a larger volume of blood than the known pulsed high pressure pumping devices which act locally only under the arch of the foot. Moreover, the gradual pressure application provided by the invention is very comfortable to the user since lower pressures are applied to a better effect. Additionally, the bladder may be held inflated for a period of time, typically 1 second to further enhance arterial flow.

The bladder 14 is deflated by exhausting the gas therein to the ambient atmosphere which occurs fairly rapidly compared to the slow rate of inflation. The bladder is again inflated typically within a range of 30 to 60 seconds, as desired, in order to maximize the hyperaemic effect for increased arterial inflow and thereby venous outflow. The inflation/deflation cycle is carried out as long as treatment is required.

A valve arrangement or similar devices, for example, solenoids may be used to control the inflation and deflation cycle. Due to the requirement for slow pressure rise time and lower pressures a compressor alone is sufficient to provide the requisite pressurized air.

The foot garment can be recommended for continual use to provide continual prophylaxis since it can be worn whilst sleeping due to its comfortable gradual compression action. The foot garment may be worn in conjunction with a calf or thigh garment for simultaneous stimulation of the venous blood flow or sequential stimulation i.e. starting from the foot, then calf, then thigh as appropriate or the foot garment may be used after actuation of a thigh or calf garment to "prime" the foot prior to its action.

What is claimed is:

1. A garment for applying compressive pressures to a foot comprising:

at least one bladder adapted to engage substantially the whole of the sole of the foot and to engage longitudinally the dorsi-medial and dorsi-lateral areas of the top of the foot;

means for positioning and securing the garment to the foot; and means to slowly inflate the bladder to provide a gradual compressive pressure to the sole and to the dorsi-medial and dorsi-lateral areas of the foot, and to cause a relatively rapid deflation of the bladder.

2. A garment as claimed in claim 1, wherein the garment includes only one bladder being flexible for wrapping around and engaging the sole, the dorsi-medial areas, and dorsi-lateral areas of the foot.

3. A garment as claimed in claim 1 wherein the at least one bladder is inflated over a period of at least 2 seconds to provide a slow rise in pressure as the gradual compressive pressure.

4. A garment as claimed in claim 1, wherein the means for inflating the bladder causes the inflated state of the bladder to be held for a period of time before the deflation thereof.

5. A garment as claimed in claim 4, wherein the inflated state is held for a period less than or equal to the duration of inflation.

6. A garment as claimed in claim 1, wherein the means for positioning and securing the garment includes a cushioning material.

7. The garment of claim 6 wherein the cushioning material includes a foam backing.

8. A garment as claimed in claim 1, wherein the garment includes:

securing means for securing portions of the garment as the bladder engages the sole and the dorsi-medial and dorsi-lateral areas of the foot.

9. A garment as claimed in claim 1, wherein the at least one bladder includes at least one aperture in the outer surface of the at least one bladder to provide ventilation to the foot during use of the garment.

10. The garment of claim 1 wherein the at least one bladder includes:

a plurality of bladders, with each bladder respectively engaging one of the whole of the sole of the foot, the dorsi-medial area of the foot, and the dorsi-lateral area of the foot.

11. A garment as claimed in any preceding claim, wherein the bladder is made from vapor-permeable material.

12. A garment as claimed in claim 11, wherein the bladder material has a greater elasticity than the garment material.

13. A method of applying cyclic compressive pressures to a foot comprising the steps of:

providing at least one bladder engaging substantially the whole of a sole of the foot and the dorsi-medial and dorsi-lateral areas of a top of the foot;

applying gradual, slow compressive pressure to the areas of the foot engaged by the bladder by slowly inflating the bladder; and rapidly releasing the pressure by rapidly deflating the bladder.

14. The method of claim 13 wherein the step of applying pressure includes the step of inflating the at least one bladder over a period of at least two seconds.

15. The method of claim 13 further comprising the step of:

causing the inflated bladder to be held in the inflated state for a period of time before releasing the pressure.

16. The method of claim 15 wherein the inflated state is held for a period less than or equal to the duration of inflation.

17. A garment as claimed in claim 1, wherein the at least one bladder is formed from two sheets of plastic material joined together at their peripheries and joined internally to define the at least one bladder, wherein the join line at the peripheries is located internally to the edge of the plastic material.

18. A garment for applying cyclic compressive pressures to a foot, the garment comprising:

at least one bladder adapted to engage substantially the whole of the sole of the foot and to engage longitudinally the dorsi-medial and dorsi-lateral areas of the top the foot;

means for positioning and securing the garment to the foot; and means for inflating and deflating the at least one bladder in predetermined cycles, including a first cycle for slowly inflating the at least one bladder to provide a gradual compressive pressure to the sole and to the dorsi-medial and dorsi-lateral areas of the foot, a second cycle for holding the at least one bladder in the inflated state, and a third cycle for causing a relatively rapid deflation of the bladder.

19. The garment of claim 18 wherein the positioning and securing means includes:

cushioning material having a foam backing.

20. The garment of claim 18 wherein the positioning and securing means includes:

a set of hook-and-loop fasteners for securing portions of the garment to the foot.

* * * * *